United States Patent [19]

Raynor

[11] Patent Number: 4,883,653

[45] Date of Patent: Nov. 28, 1989

[54] ARYL N,N-BIS CINNAMAMIDE COMPOUNDS AND THEIR USE AS ULTRAVIOLET LIGHT STABILIZERS

[75] Inventor: Robert J. Raynor, North Branford, Conn.

[73] Assignee: Olin Corporation, Cheshire, Conn.

[21] Appl. No.: 623,859

[22] Filed: Jun. 25, 1984

[51] Int. Cl.$^4$ .................. A61K 31/165; C07C 103/78; C07C 103/76

[52] U.S. Cl. ...................................... 424/60; 564/155; 564/158; 514/616; 523/508; 524/217; 524/220; 524/225; 524/226

[58] Field of Search ................. 564/158, 155; 514/616; 424/59, 60; 523/508; 524/217, 220, 225, 226

[56] References Cited

U.S. PATENT DOCUMENTS

| | | |
|---|---|---|
| 3,936,418 | 3/1976 | Pond et al. .................. 260/45.8 NT |
| 3,941,581 | 3/1976 | Teach ............................. 564/155 X |
| 4,049,713 | 9/1977 | Spivack ............................. 564/158 |
| 4,127,586 | 11/1978 | Rody et al. ..................... 260/308 B |

FOREIGN PATENT DOCUMENTS 2349480  4/1975  Fed. Rep. of Germany .

OTHER PUBLICATIONS

CA. 78:1361661(b), (1973).
CA. 69:67276n, (1968).
CA 45:7969e, (1951).
Altman et al., *J. Pharm. Sci.*, 1972, 61(4), 610–613.
Cerbai et al., *Gazz. Chim. Ital.*, 92, 420–427, (1962).

*Primary Examiner*—Charles E. Warren
*Assistant Examiner*—Carolyn S. Elmore
*Attorney, Agent, or Firm*—Dale L. Carlson; William A. Simons

[57] ABSTRACT

An aryl N,N'-bis cinnamamide compound having a formula comprising:

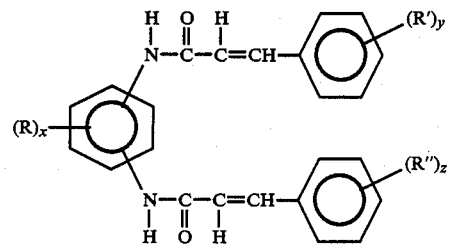

wherein x equals an integer from 0 to 3; y equals an integer from 0 to 2; z equals an integer from 0 to 2; each R is individually selected from the group consisting of a lower alkyl group having 1 to 4 carbon atoms, a lower alkoxy group having from 1 to 4 carbon atoms, a halo group, a nitro group, an aryl group having 6 to 18 carbon atoms, and a fused unsubstituted or substituted aromatic ring when x is 2 or 3; and each R' and R" is individually selected from the group consisting of a lower alkyl group having from 1 to 4 carbon atoms, a lower alkoxy group having from 1 to 4 carbon atoms, a halo group, a nitro group or an aryl group having from 6 to 18 carbon atoms. These compounds are useful as U.V. light absorbers in plastics and cosmetics (e.g. sunscreens).

5 Claims, No Drawings

ARYL N,N-BIS CINNAMAMIDE COMPOUNDS AND THEIR USE AS ULTRAVIOLET LIGHT STABILIZERS

BACKGROUND OF THE INVENTION

1. Field of the Invention

This invention relates to selected aryl N,N'-bis cinnamamide compounds and their use as ultraviolet light stabilizers.

2. Description of the Prior Art

Ultraviolet (UV) radiation having wave lengths from about 280 to about 400 nm may cause the degradation of exposed organic matter such as plastics and will burn and/or induce tumors in human skin. To negate these undesirable actions, plastics and the like are protected by chemical additives called UV stabilizers and the human skin and hair is protected by cosmetics containing UV stabilizers (e.g. sunscreens).

To be viable for commercial applications, a UV stabilizer should preferably have a strong ultraviolet light absorptivity at wave lengths between 280 and 400 nm, be photostable by itself, be compatible with the substrate (e.g. plastic or cosmetic emulsion) in which it is used as an additive, be non-volatile at the high temperatures involved during incorporation and processing stages as well as during certain end uses, possess low color, be chemically inert, have low or no toxicity or skin sensitization/irritation properties, be non-mutagenic, and be stable to the environments experienced during its processing and application. Furthermore, for human sunscreen use, it is also desirable that the UV stabilizer be relatively insoluble in water.

Accordingly, it is an object of the present invention to provide a novel class of UV light stabilizer compounds.

A specific object of this invention is to provide a novel class of UV light stabilizer compounds which may be used to stabilize ultraviolet degradable organic compositions against deterioration resulting from the exposure to such UV radiation.

Another specific object is to provide a novel class of UV light stabilizer compounds which may be used in human cosmetic products such as sunscreens, hair dyes and hair tinting compositions to prevent or retard UV radiation from penetrating the human skin or hair.

These and other objects and features of the invention will be made apparent from the following more particular description of the invention.

BRIEF SUMMARY OF THE INVENTION

The present invention, therefore, is directed to aryl N,N'-bis cinnamamide compounds having formula (I):

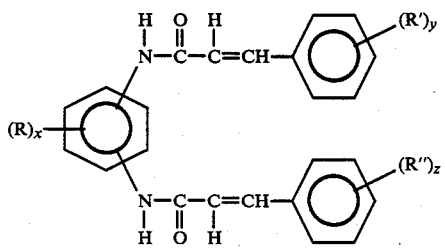

wherein x equals an integer from 0 to 3; y equals an integer from 0 to 2; z equals an integer from 0 to 2; each R is individually selected from the group consisting of a lower alkyl group having 1 to 4 carbon atoms, a lower alkoxy group having from 1 to 4 carbon atoms, a halo group, a nitro group, an aryl group having 6 to 18 carbon atoms, and a fused unsubstituted or substituted aromatic ring when x is 2 or 3; and each R' and R" is individually selected from the group consisting of a lower alkyl group having from 1 to 4 carbon atoms, a lower alkoxy group having from 1 to 4 carbon atoms, a halo group, a nitro group or an aryl group having from 6 to 18 carbon atoms.

Also, the present invention is directed to organic compositions susceptible to ultraviolet degradation being stabilized against such degradation with an effective stabilizing amount of an aryl N,N-bis cinnamamide compound having formula (I) above.

Still further, the present invention is directed to a process for stabilizing an organic composition susceptible to ultraviolet degradation comprising incorporating into said organic composition an effective stabilizing amount of an aryl N,N'-bis cinnamamide compound having formula (I), above.

Furthermore, the present invention is directed to human sunscreen compositions which effectively prevent or retard UV light from penetrating human skin or hair, said sunscreen compositions comprising an effective screening amount of an aryl N,N'-bis cinnamamide compound having formula (I), above.

And even further, the present invention is directed to a process for substantially screening out UV light from human skin or hair comprising applying a sunscreen composition on said skin or hair to prevent or retard UV light from penetrating to said skin or hair, said sunscreen composition comprising an effective screening amount of an aryl N,N'-bis cinnamamide compound of formula (I), above.

DETAILED DESCRIPTION

These aryl N,N'-bis cinnamamides (also known as N,N'-dicinnamoyl-aryldiamines) of the present invention may be made by reacting 1 mole of the corresponding aryldiamine compound with 2 moles of a selected cinnamoyl acid chloride, preferably in the presence of a solvent such as 1,4-dioxane and an acid scavenger such as pyridine and at a reaction temperature from about 20° C. to about 50° C. This reaction is illustrated by the formation of N,N'-dicinnamoyl-2,4-toluenediamine by the reaction of 1 mole of 2,4-toluenediamine with 2 moles of cinnamoyl chloride as shown in the following equation (A):

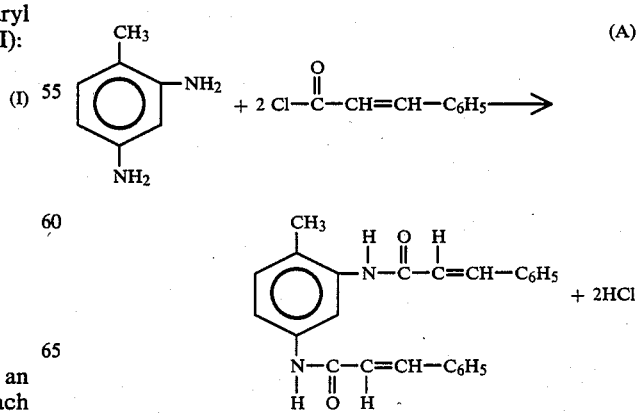

These aryldiamine precursors may be unsubstituted (x=O) or contain from 1 to 3 substituents (x=1 to 3) of the selected classes mentioned above. Suitable lower alkyl substituents included methyl, ethyl, n-propyl, isopropyl, n-butyl, t-butyl and isobutyl groups. Corresponding alkoxy groups may be also suitable. Halo groups include fluoro, chloro, bromo, and iodo groups. Suitable aryl groups include unsubstituted phenyl groups and alkyl-substituted phenyl groups. Furthermore, these aryldiamine compounds include fused ring compounds such as unsubstituted naphthalene or alkyl-substituted napthalenes. Because of cost considerations, it is now preferred to employ various toluenediamine (x=1, R=CH$_3$) or phenylenediamine (x=O) as the aryldiamine precursors.

Representative aryldiamine compounds which may be used as precursors for the compounds of the present invention include:
ortho-phenylenediamiane
2,3-toluenediamine
2,4-toluenediamine
2,5-toluenediamine
2,6-toluenediamine
3,4-toluenediamine
3,5-toluenediamine
4,5-dimethyl-ortho-phenylenediamine
diaminonaphthalene These cinnamoyl acid chlorides may include unsubstituted cinnamoyl groups (y=O, z=O) or contain from 1 or 2 substituents (y=1 to 2, z=1 to 2) of the selected classes mentioned above. Suitable lower alkyl substituents include methyl, ethyl, n-propyl, isopropyl, n-butyl, t-butyl and isobutyl groups. Corresponding lower alkoxy groups may be also suitable. Halo groups include fluoro, chloro, bromo, and iodo groups. Suitable aryl groups include unsubstituted phenyl groups and alkyl-substituted phenyl groups. It is preferred, that the same cinnamoyl group (where R' and R" are the same) be added to each amine group on the aryl diamine precursor because then only one reaction step is needed. However, it may be desirable in certain instances to employ different cinnamoyl moieties. Most preferably, it is now desired to employ unsubstituted cinnamoyl moieties (y=z=O).

Representative cinnamoyl acid chlorides which also may be used as precursors for the compounds of the present invention include:
cinnamoyl chloride
p-methyl cinnamoyl chloride
2,5-dimethoxycinnamoyl chloride
3,4-dimethoxycinnamoyl chloride
o-nitrocinnamoyl chloride
m-nitrocinnamoyl chloride
p-nitrocinnamoyl chloride
2-methyl-4-nitrocinnamoyl chloride
4-methyl-3-nitrocinnamoyl chloride Any conventional reaction conditions employed for the reaction between an amine compound with an acid chloride are the preferred synthesis parameters for the compounds of the present inventions. However, the present invention is not intended to be limited to any particular reaction conditions or precursors. Alternatively, cinnamic acid esters or anhydrides may be employed. Advantageously and preferably, the reaction is carried out with a 2:1 mole ratio of the cinnamoyl chloride precursor(s) to the aryldiamine precursor in the presence of a suitable inert solvent and an acid scavenger. Preferred solvents include 1,4-dioxane, tetrahydrofuran, hexane and the like. Preferred acid scavengers include pyridine and triethylamine and the like. However, the use of a solvent or an acid scavenger, or both, is only desirable, but not necessary. The reaction temperature and time will both depend upon many factors including the specific reactants used. In most situations, reaction temperatures may advantageously be from about 20° C. to about 50° C. and reaction times from about 15 minutes to about 300 minutes or more may be preferred. The product may be recovered from the reaction mixture by any conventional means such as filtration, extraction or the like. The product may be further purified by conventional means such as recrystallization in an inert solvent or the like.

The compounds of the present invention are believed to possess a combination of properties which make them advantageous as UV stabilizers. These desirable properties include their white or near-white color, their nonvolatility, their stability under normal storage conditions, their insolubility in water but solubility in certain organic solvents, their exceptionally strong maximum absorptivity of UV light from about 280 to about 320 nm wave lengths as well as their low order of toxicity as exemplified by the data given below in the Examples.

Also in accordance with the present invention, it has been found that the compounds of formula (I) above may be utilized as effective ultraviolet stabilizers for UV degradable organic material or in human sunscreen compositions. In practicing the use as a UV stabilizer for such organic materials, an effective stabilizing amount of one or more of these compounds is incorporated into the organic composition susceptible to UV degradation. In practicing the use as a UV stabilizer in human sunscreen composition, an effective screening amount of one or more compounds of formula (I) is incorporated into the sunscreen composition which is applied to human skin or hair. It is to be understood that the terms "effective stabilizing amount" and "effective screening amount" as used in the specification and claims herein is intended to include any amount that will prevent or retard UV radiation from either degrading the organic material incorporated therein or penetrating the human skin or hair, respectively. Of course, these amounts may be constantly changing because of possible variations in many parameters. Generally, amounts from about 0.01% to about 10%, by weight, based on the weight of the organic or carrier material to which they are added. While a detectable amount of stabilization or screening may be obtained with amounts less than 0.01%, this amount of stabilization or screening would be of little practical utility in a commercial application. Moreover, while amounts greater than 10% by weight provide effective ultraviolet stability and screening, such concentrations are undesirable because of cost and the deleterious effect which such concentrations may have on the mechanical properties of the organic composition in which the UV stabilizer is incorporated. Preferably, the stabilizer is used in an amount of from about 0.1% to about 3% by weight.

Possible organic materials which are susceptible to UV degradation and which may have the compounds of formula (I) incorporated therein as UV stabilizers include organic polymers (both thermoplastic and thermosetting polymers). Wholly synthetic polymers such as addition polymers, condensation polymers and condensation polymers crosslinked by addition polymerization may be aided with these UV stabilizers. Natural polymers such as polysaccharides, rubber and proteins may also be aided. Also, chemically modified polymers may be employed as substrates as well as other substances such as natural and synthetic light-sensitive waxes, fats and oils, emulsions which contain light-sensitive fatty substances or the abovementioned polymers.

Exemplary lists of these polymers and other substances are shown in U.S. Pat. No. 4,127,586, which issued to Rody et al on Nov. 28, 1978, and U.S. Pat. No. 3,936,418, which issued to Pond et al on Feb. 3, 1976. Both of these U.S. Patents are incorporated herein by reference in their entireties.

Any suitable carrier material which is presently used for human sunscreen compositions may have the compounds of formula (I) incorporated therein. Examples of this carrier material for sunscreens include emollients or emulsions of conventional cosmetic chemicals known in the art.

Such organic compositions and sunscreen compositions may contain further additives, pigments, colorants, stabilizers and the like. These may include antioxidants, other UV stabilizers and sunscreens, metal like.

These aryl N,N'-bis cinnamamide compounds of formula (I) may be incorporated into these organic compositions or sunscreen compositions by any convention blending technique such as melt-blending, mixing or the like. Alternatively, they may add on the surface of such materials or adfixed thereto by means of a gel or the like.

The following examples further illustrate the present invention. All parts and percentages employed therein are by weight unless otherwise indicated.

EXAMPLE 1

Preparation of N,N'-Dicinnamoyl-2,4-Toluenediamine

In a 1 liter, 4 neck, flask equipped with a mechanical stirrer, thermometer, water condenser, and dropping funnel was placed 36.9 grams (0.3 moles) 2,4-toluenediamine, 48 grams pyridine, and 150 milliliters 1,4-dioxane. The flask and its contents were then cooled to 25° C. by means of an ice-water bath. To this cooled and stirred mixture was added by means of the dropping funnel a solution of 100 grams (0.6 moles) cinnamoyl chloride in 100 milliliters 1,4-dioxane. The addition required 0.5 hr. during which time the temperature of the flask and its contents was maintained between 25°-30° C. Upon completion of the addition the contents of the flask were allowed to stir at 25°-30° C. for an additional 0.5 hr. then poured into 500 milliliters of cold water which immediately caused the precipitation of light amber color solids. The solids were collected by suction filtration, partially dried, and recrystallized from 1,4-dioxane giving 98.0 grams (85.5%) of light lemon color crystals. Recrystallization of this material from ethyl alcohol containing powdered charcoal gave 74 grams (64.6% yield) of pure white crystals which melted at 217°-219° C.

Nuclear magnetic resonance spectroscopy and elemental analysis confirmed the product to be N,N'-dicinnamoyl-2,4-toluenediamine.

EXAMPLE 2

Preparation of N,N'-Dicinnamoyl-ortho-Phenylenediamine

The procedure of Example 1 was repeated except ortho-phenylenediamine [5.41 grams (0.05 moles)] and 7.9 grams of pyridine were placed in a flask containing 100 milliliters of 1,4-dioxane. After cooling and stirring as before, a solution of cinnamoyl chloride [16.66 grams (0.1 mole)] dissolved in 100 milliliters of 1,4-dioxane was added to the flask. Upon completion of the reaction and following the recovery and recrystallization step as before, dried buff-colored crystals weighing 10.1 grams (55% yield) were collected which had a melting point of 212.3° C.

Elemental analysis was consistent with N,N'-dicinnamoyl-ortho-phenylenediamine.

EXAMPLE 3

Preparation of N,N'-dicinnamoyl-4,5-dimethyl ortho-phenylenediamine

The procedure of Example 1 was again repeated except 4,5-dimethyl-ortho-phenylenediamine [6.81 grams (0.05 moles)] and 7.9 grams of pyridine were placed in a flask containing 100 milliliters of 1,4-dioxane. After cooling and stirring as before, a solution of cinnamoyl chloride [16.6 grams (0.1 mole)] dissolved in 100 milliliters 1,4-dioxane was added to the flask. Upon completion of the reaction and following the same recovery and recrystallization steps as before, dried white crystals weighing 10.7 grams (54% yield) were collected which had a melting point of 243.5° C.

Elemental analysis was consistent with N,N'-dicinnamoyl-4,5-dimethyl-ortho- phenylenediamine.

EXAMPLE 4

Preparation of N,N'-di(p-methylcinnamoyl)-2,4-toluenediamine

The procedure of Example 1 was repeated except that p-methyl cinnamic acid [8.0 grams (0.05 moles)] was added to the flask. Then, $SOCl_2$ [8.9 grams (0.075 moles)] in 30 milliliters benzene was added to form the acid chloride. Next, 2,4-toluenediamine [3.05 grams, (0.025 moles)] in 100 milliliters of benzene and 4.0 grams of pyridine was added to the flask. Upon completion of the reaction and following the recovery and recrystallization (in THF/hexane) steps, white crystals weighing 6 grams (60% yield) were collected which had a melting point of 251.7° C.

Elemental analysis was consistent with N,N'-di(p-methylcinnamoyl)-2,4-toluenediamine.

EXAMPLE 5

Preparation of N,N'-dicinnamoyl-2,3-diaminonaphthalene

The procedure of Example 1 was repeated except that 2,3-diaminonapthalene [50 grams (0.03 moles)] and 4.8 grams of pyridine were placed in a flask containing 100 milliliters of 1,4-dioxane. After cooling and stirring as before, a solution of cinnamoyl chloride [10 grams (0.06 moles)] dissolved in 55 milliliters of 1,4-dioxane was added to the flask. Upon completion of the reaction and following the recovery and recrystallization (in glacial acetic acid), white crystals weighing 7.5 grams (60% yield) were collected which had a melting point of 276.4° C.

Elemental analysis was consistent with N,N'-dicinnamoyl-2,3-diaminonaphthalene.

EXAMPLE 6

Preparation of N,N'-dicinnamoyl-3,4-toluenediamine

The procedure of Example 1 was repeated except 3,4-toluenediamine [36.9 grams (0.03 moles)] and 48 grams of pyridine were placed in a flask containing 150 milliliters of 1,4-dioxane. After cooling and as before, a solution of cinnamoyl chloride [100 grams (0.60 moles)] dissolved in 100 milliliters of 1,4-dioxane was added to the flask. Upon completion of the reaction and following the recovery and recrystallization steps as before, white crystals weighing 9.2 grams (65% yield) were collected which had a melting point of 218° C.

Elemental analysis was consistent with N,N'-dicinnamoyl-3,4-toluenediamine.

The ultraviolet light absorptivity properties of the compounds of Examples 1-6 were measured by means of a spectrophotometer and are given in Table I. A comparison is also given for paraaminobenezonic acid (PABA), which is a well known UV stabilizer. This data indicates that all of these compounds of the present invention are very good ultraviolet absorbers. The photostability of the compound of Example 1 was also measured by subjecting a solution of the compounds to the UV radiation produced by a 450 watt medium pressure mercury lamp at 17°-25° C. in a Hanovia photochemical apparatus and periodically determining its absorbance by means of a spectrophotometer. The data as shown in Table II indicates excellent photostability.

TABLE I

| Example | Wave Length (λ), max. | Absorptivity (l/g · cm)[1] | Molar Absorptivity[2] |
|---|---|---|---|
| 1 | 292 | 130.8 | 49,966 |
| 2 | 282 | 154.8 | 57,262 |
| 3 | 282 | 139.5 | 55,539 |
| 4 | 305 | 152.7 | 62,922 |
| 5 | 284 | 158.2 | 66,433 |
| 6 | 282 | 154.8 | 59,443 |
| PABA | 290 | 132.8 | 18,200 |

[1]Measured on a Perkin-Elmer spectrophotometer, Model No. 330.
Absorptivity (a) equals $\frac{A}{bc}$ where A = absorbance (also called optical density) and is an observed (experimental determined) value;
b = cell size; and
c = concentration of compound in solvent.
[2]Molar Absorptivity = absorptivity (a) times molecular weight.

TABLE II

| Time (hrs.) | Absorbance (A) at 292 nm |
|---|---|
| 0 | 1.31 |
| 0.4 | 1.29 |
| 1.2 | 1.27 |
| 2.9 | 1.28 |
| 6.3 | 1.26 |

TOXICITY TESTS

The oral LD$_{50}$ in rats for N,N,-dicinnamoyl-2,4-toluenediamine was greater than 5 grams/Kg of body weight. No signs of toxicity nor deaths occurred at this dose, equivalent to a human ingesting approximately 350 grams of the compound. The dermal LD$_{50}$, determined by applying a 2 g/Kg of body weight dermal dose of this compound to the backs of rabbits for a 24 hour contact period, was greater than 2 g/Kg of body weight. No deaths occurred over the 14 day observation period.

Tests to determine the inhalation LC$_{50}$ in rats, by inhalation of 200 mg of compound per liter of air for one hour, produced no deaths. The LC$_{50}$ is greater than 200 mg/l.

This compound was not a skin sensitizer at a 50% by weight concentration in guinea pigs. It was a mild skin irritant in rabbits and an eye irritant in rabbits.

In summary, this toluenediamine derivative is not considered by the Federal Hazardous Substances guidelines to be toxic by ingestion, dermal exposure, nor inhalation exposure. This is important because in the factor situation, exposure to the compound is most likely to occur by ingestion, dermal contact or by inhalation.

MUTAGENIC TEST

N,N'-dicinnamoyl-2,4-toluenediamine was analyzed for mutagenic activity using the standard short term bacterial test for genetic toxicity called the Ames Salmonella/Microsome Plate Assay. The test was conducted in five strains of Salmonella, with an without metabolic activation, at concentrations of 1, 3, 10, 30 and 100 micrograms of the compound per plate.

The compound did not induce significant mutation in any of the strains, either in the presence or absence of metabolic activation. Under the conditions of this assay, the compound is not considered mutagenic.

What is claimed is:

1. An organic composition susceptible to ultraviolet degradation stabilized against such degradation with an effective stabilizing amount of an aryl N,N'-bis cinnamamide compound having the formula:

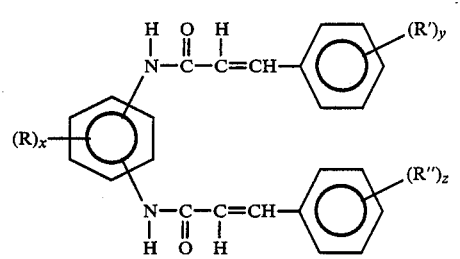

wherein x equals an integer from 1 to 3; y equals an integer from 0 to 2; z equals an integer from 0 to 2; each R is individually selected from the group consisting of a lower alkyl group having 1 to 4 carbon atoms, a lower alkoxy group having from 1 to 4 carbon atoms, a nitro group, an aryl group having 6 to 18 carbon atoms; and each R' and R" is individually selected from the group consisting of a lower alkyl group having from 1 to 4 carbon atoms, a lower alkoxy group having from 1 to 4 carbon atoms, a halo group, a nitro group or an aryl group having from 6 to 18 carbon atoms.

2. The organic composition of claim 1 wherein said organic composition is an organic polymer.

3. A sunscreen composition which effectively prevents UV light from penetrating human skin or hair said sunscreen composition comprising a human sunscreen carrier and an effective screening amount of an aryl N,N'-bis cinnamamide compound having the formula:

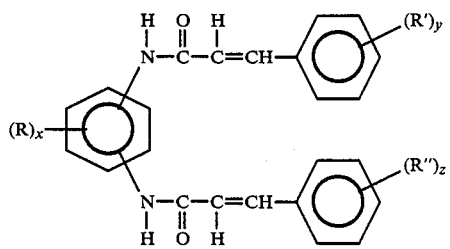

wherein x equals an integer from 1 to 3; y equals an integer from 0 to 2; z equals an integer from 0 to 2; each R is individually selected from the group consisting of a lower alkyl group having 1 to 4 carbon atoms, a lower alkoxy group having from 1 to 4 carbon atoms, a nitro group, an aryl group having 6 to 18 carbon atoms; and each R' and R" is individually selected from the group consisting of a lower alkyl group having from 1 to 4 carbon atoms, a lower alkoxy group having from 1 to 4 carbon atoms, a halo group, a nitro group or an aryl group having from 6 to 18 carbon atoms.

4. An aryl N,N'-bis cinnamamide compound having the formula:

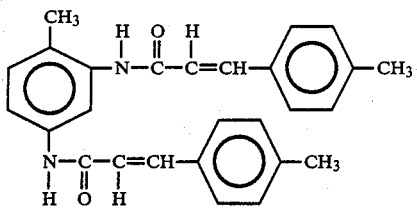

5. An aryl N,N'-bis cinnamamide compound having the formula:

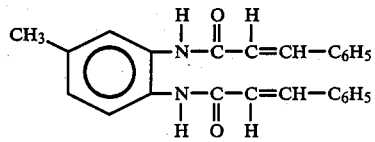

* * * * *